United States Patent [19]
Komoto et al.

[11] Patent Number: 4,895,844
[45] Date of Patent: Jan. 23, 1990

[54] INDOLE ALKALOID COMPOSITIONS AND THEIR METHODS OF USE

[75] Inventors: Shigeo Komoto; Oliver J. McConnell, both of Vero Beach, Fla.

[73] Assignee: Harbor Branch Oceanographic Institution, Inc., Ft. Pierce, Fla.

[21] Appl. No.: 313,281

[22] Filed: Feb. 23, 1989

Related U.S. Application Data

[63] Continuation of Ser. No. 30,670, Mar. 25, 1987, abandoned.

[51] Int. Cl.$^4$ .................. A61K 31/495; C07D 403/14
[52] U.S. Cl. ...................................... 514/254; 544/373
[58] Field of Search ................ 514/252, 254; 544/373

[56] References Cited

U.S. PATENT DOCUMENTS 3,577,423  5/1971  Archibald et al. .................. 544/373
4,631,149 12/1986  Rinehart, Jr. et al. ............. 540/579

OTHER PUBLICATIONS

Akkerman et al., *Rec. Trav. Chim.*, 73, pp. 629–648, (1954).

*Primary Examiner*—Mukund J. Shah
*Assistant Examiner*—E. Bernhardt
*Attorney, Agent, or Firm*—Carroll F. Palmer

[57] ABSTRACT

This invention relates to novel compositions which are useful as antitumor compositions, a process of producing the compositions and a method for inhibiting tumors, utilizing the compositions. More particularly, the novel compositions are indole alkaloid compositions which are derived from marine sponges of the family Biemnidae.

8 Claims, No Drawings

INDOLE ALKALOID COMPOSITIONS AND THEIR METHODS OF USE

This application is a continuation of application Ser. No. 030,670, filed Mar. 25, 1987, now abandoned.

FIELD OF THE INVENTION

This invention relates to a new organic compositions which have useful antitumor activity. Additionally and particularly, this invention relates to a new antitumor indole alkaloid compositions derived from a marine organism, i.e., a sponge of the Oragmacidon sp. and their methods of use.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or of the host's body as a whole.

Tumors inflict mammals and man with a variety of disorders and conditions including various forms of cancer and resultant cancerous cachexia Cancerous cachexia refers to the symptomatic discomfort that accompanies the infliction of a mammal with a tumor. These symptoms include weakened condition of the inflicted mammal as evidenced by, for example, weight loss. The seriousness of cancer is well know, e.g., cancer is second only to heart and vascular diseases as a cause of death in man.

Considerable research and resources have been devoted to oncology and antitumor measures including chemotherapy. While various antitumor agents and methods have been developed which aid in inhibiting tumors additional methods and chemical agents are needed.

A potential source for antitumor compositions is marine plant and animal life and of particular interest are marine sponges. It has now been found that an organic composition derived from extracts of a sponge of the Dragmacidon sp. possess useful antitumor activity.

SUMMARY OF THE INVENTION

It is therefore an object of the invention to provide novel compositions which are useful as antitumor agents and a process for producing such novel compositions.

It is an additional object of the invention to provide a method for inhibiting tumors and resultant infection and disease utilizing novel antitumor compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described here, the invention comprises compositions of the formula:

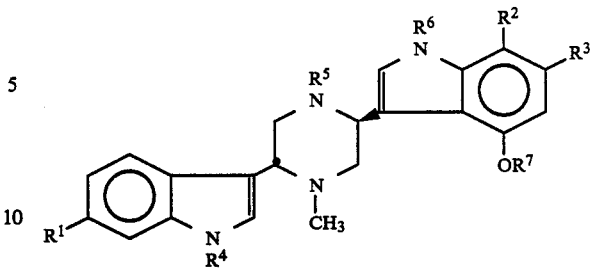

wherein $R^{1-3}$ are the same or different and are a hydrogen or halogen and $R^{4-7}$ are the same or different and are a hydrogen, lower alkyl or lower acyloxy group. In preferred embodiments $R^{1-3}$ are a hydrogen or bromine and $R^{4-7}$ are a hydrogen, methyl acetyloxy group.

In a further preferred embodiment the composition has the formula:

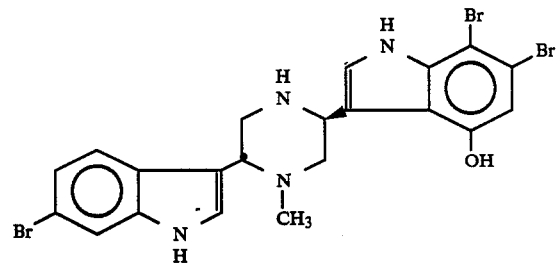

In preferred embodiments of the invention, the composition is substantially pure.

As embodied and fully described herein, the invention also comprises antitumor compositions comprising, as active ingredient, an effective antitumor amount, respectively, of the compositions of the invention and a non-toxic pharmaceutically acceptable carrier or diluent.

As embodied and fully described herein, the invention also comprises a process to produce the compositions of the invention. The process comprises the steps of collecting marine sponge of the Dragmacidon sp. contacting the marine sponge with a suitable organic solvent system to obtain an extract; fractionating the extract; and isolating indole alkaloid compositions of the invention from the fractionated extract.

A current taxonomic identification of the sponge from which the novel compounds of the invention were extracted is:
Phylum Porifera
  Class Demospongiae
    Order Axinellida
      Family Axinellidae
        Genus Dragmacidon The sponge has not been described to species in the literature. As time passes, it is to be expected that this sponge will be taxonomically described to the species level and those skilled in the art will be able to identify it in its habitat and elsewhere without need to refer to voucher specimens, i.e., simply by genus and species identification.

Identification of the sponge to the family Axinellidae and genus Dragmacidon was made by Dr. R. W. M. Van Soest (Institute for Taxonomic Zoology, University of Amsterdam).

A description of the Genus Dragmacidon can be found in the following published references:

Hallman, E. F. 1917. A revision of the genera with microscleres included, or provisionally included, in the family Axinellidae; with descriptions of some Australian species; Part III. *Proceedings of the Linnaean Society of New South Wales*, 41: 634–675.

The sponge Dragmacidon sp. is dark brown both alive and preserved in ethanol. The consistency is brittle and non-compressible. The ectosome is a heavy organic skin with foreign material. The choanosome is fibrous, with sparse dendritic-plumose spicule tracts. Spicules are trichodragmata and styles, 400–520 μm in length by 7–10 μm in width.

Identification of the sponge to the family Axinellidae and genus Dragmacidon is based on microscopic examination of a taxonomic voucher specimen. A similar voucher specimen is deposited at the Indian River Coastal Zone Museum (Catalog No. 003:00039), Harbor Branch Oceanographic Institution, Inc., Ft. Pierce, Fla. (HBOI/DBMR number 2-VI-84-3-15). The sponge in the voucher specimen is preserved in 70% ethanol with an expected shelf life of at least 30 years and is accessable to those skilled in the art for identification purposes.

The sponge Dragmacidon sp. was collected from southeast Grand Bahama Island (lattitude 26°28.75' N, longitude 77°53.50 W) at a depth of 480 ft. on a rock and sand slope. The sample was collected by manned submersible equipped with a color video camera, a multi-function manipulator arm and containers to hold the sample. With color video, the sponge appears dark gray-brown. It is not common.

The sponge was initially incorrectly identified as family Biemnidae. A more detailed taxonomic examination of the voucher specimens of the sponge led to the currently correct identification as Dragmacidon sp. The reason for this identification error was due to the fact that the sponge was originally misidentified as an undescribed species in the family Biemnidae. This incorrect identification was based only on spicule complement without regard to skeletal arrangement of ectosome and choanosome. Assignment of the sponge to the family Axinellidae, genus Dragmacidon was made after more detailed examination of the skeleton.

As embodied and fully described herein, the invention further comprises a method for inhibiting tumors comprising contacting tumor cells with an effective antitumor amount of the composition of the invention.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, an example of which is illustrated in the following example section.

In accordance with the invention novel compositions are provided to achieve the objects in accordance with the purposes of the invention, as embodied and fully described herein, the invention comprises indole alkaloid compositions of the general formula I:

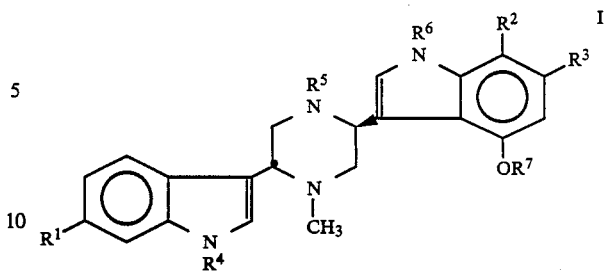

wherein $R^{1-3}$ are the same or different and are a hydrogen and halogen and $R^{4-7}$ are the same or different and are a hydrogen, lower alkyl or lower acetyloxy group. In preferred embodiments $R^{1-3}$ are hydrogen or bromine and $R^{4-7}$ are a hydrogen, methyl or acetyloxy group.

In a further preferred embodiment invention the composition has the formula, shown below, and is named biemnidin:

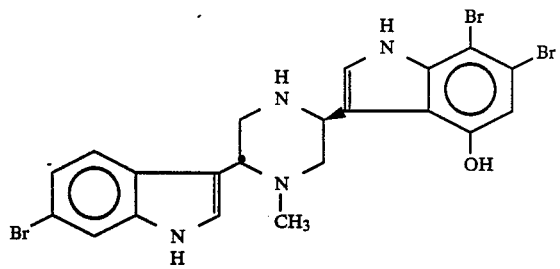

In preferred embodiments of the invention, the composition is substantially pure.

In accordance with the invention, an antitumor composition is provided comprising as active ingredient an effective antitumor amount of the composition of the invention and a non-toxic pharmaceutically acceptable carrier or diluent. While effective amounts may vary, as conditions in which an antitumor composition is used vary, a minimal dosage required for in vitro activity is generally between 0.01 and 100 micrograms per milliliter against $10^5$ tumor cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor amount of the composition of the invention. The composition of the invention is active for inhibiting a diverse range of tumors including, but not limited to P388 mouse leukemia cells, human lung, colon and mammary tumors such as lung carcinoma A-549, ileocecal adenocarcinoma HCT-8, and human breast adenocarcinoma cells MD-AMB-231. The effectiveness of the composition of the invention for inhibiting tumors cells and tumors indicates its usefulness for controlling tumors in hosts including mammals and for treating cancerous cachexia.

In accordance with the invention, a process is provided to produce the compositions of the invention. The process comprises the steps of collecting samples of marine sponge of the family Biemnidae; contacting the marine sponge with a suitable organic solvent system to obtain an extract; partitioning said extract by chromatography to obtain a number of fractions; and isolating the composition of the invention from the fractionated extract.

In preferred embodiments of the invention the suitable organic solvent system is selected from the group of solvents consisting of methanol, toluene, heptane, hexanes, isooctane, acetone, ethyl acetate benzene, diethyl ether, t-butyl-methyl ether, ethanol, isopropanol, chloroform, 1,2-dichloroethane, dichloromethane, and mixtures thereof. A particularly preferred extracting solvent is a mixture of methanol and toluene.

While those solvents listed above are the presently preferred choices for the solvents useful in accordance with the invention, other suitable solvents may be substituted. A suitable solvent system should be capable of extracting the composition of the invention from other components of the sponge. Different ratios of solvents and any combination may be used in the solvent system of the invention as would be known to those skilled in the art.

Compositions according to the invention are synthesized and/or isolated by various fractionation, and chromatographic techniques from the extracts obtained. Any suitable fractionation and isolation technique, as known to those skilled in the art, may be utilized in accordance with the process of the invention. Preferred isolation techniques include various chromotography techniques such as vacuum liquid chromotography with suitable columns as would be known to those skilled in the art (e.g., Kiesel gel 60-H) eluted with a suitable solvent such as, for example, methylene chloride, isopropanol, heptane, methanol, ethanol, dichloromethane, ethyl acetate, hexanes, isooctane, dichloromethane, 1,2-dichloroethane, benzene, toluene, t-butyl-methyl ether, diethyl ether, acetone, and mixtures thereof. Particularly preferred eluents are methylene chloride and isopropanol and mixtures thereof.

A more detailed description and explanation of a preferred embodiment of the process of the invention to produce the composition of the invention is provided in the examples section.

It is therefore apparent that the composition of the invention, the process for producing the composition of the invention and the methods for utilizing the composition of the invention to inhibit tumors, viruses and fungus growth fulfill the objects of the invention.

EXAMPLE

The invention will now be illustrated by example. The example is not intended to be limiting of the scope of the present invention. In conjunction with the detailed and general description above, the example provides further understanding of the present invention and outlines a process for producing the compositions of the invention.

The following example represents a preferred embodiment of the compositions, processes and methods of the invention for satisfying the stated objects of the invention. The starting materials and reagents in the example whose methods of preparation are not indicated are commercially available from sources known to the art such as chemical supply houses.

EXAMPLE 1

Preparation of biemnidin

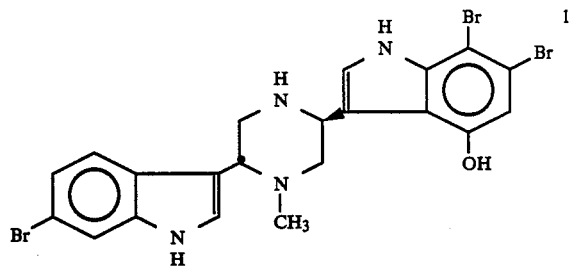

The marine sponge family Biemnidae was collected at a depth of 480 feet in Sweeting, Bahamas. An extract of the sponge was prepared by homogenizing the frozen organism and repeatedly steeping with methanol/toluene (3:1). 0.5 gms. of crude extract was chromatographed by vacuum liquid chromatography on Kiesel gel 60 (EM Science) using $CHCl_3$/isopropanol as the eluent. 90 milligrams of pure biemnidin (1) was eluted in fraction 2.

| Fraction | Eluent | Weight (mg) |
| --- | --- | --- |
| 1 | $CHCl_3$/i-PrOH = 5:1 | 230 |
| 2 | $CHCl_3$/i-PrOH = 1:1 | 90 |

Biemnidin has structure 1. It is a slightly white brown powder. The physical and spectral characteristics of 1 are listed below. $[\alpha]_D^{20} - 3°$ (C=13.2, acetone)

IR KBr; $cm^{-1}$ 3420, 3380, 3010, 2950, 2840, 2790, 1700, 1610, 1540, 1470, 1450, 1400, 1330, 1280, 1210.

UV: MeOH; $\tau max(nm)$ 220 ($\epsilon=52600$), 275 ($\epsilon=11700$), 286 sh, ($\epsilon=10900$), 293, sh, ($\epsilon=10100$).

MS: HRFAB; 580.9173 for $C_{21}H_{20}Br_3N_4O$ ($M^+ + H$) ($\Delta 2.4$)

NMR: 360 MHz in acetone-$d_6$

Proton: $\delta$ 10.8 (br, s, 1H), 10.5 (br, s, 1H), 7.84 (d, J=8.6, 1H), 7.59 (d, J=1.8, 1H) 7.36 (d, J=1.8, 1H), 7.27 (S, 1H), 7.13 (dd, J=1.8 and 8.6, 1H), 6.70 (S, 1H), 4.35 (dd, J=2.3 and 10.3, 1H), 3.46 (dd, J=3.9 and 11.3, 1H), 3.33 (dd, J=11.3 and 11.9, 1H), 3.13 (dd, J=2.3 and 11.9, 1H), 3.05 (br, 1H), 2.39 (dd, J=10.3 and 11.0, 1H), 2.04 (s, 3H).

Carbon: $\delta$ 153.1(s), 138.7(s), 138.1(s), 126.2(s), 125.3(d), 122.6(d), 122.4(d), 122.2(d), 118.5(s), 118.2(s), 117.7(s), 115.7(s), 115.4(s), 115.2(d), 110.5(d), 95.6(s), 63.4(t), 61.8(d), 53.4(d), 52.4(t), 43.8(q).

ANTITUMOR ACTIVITIES OF THE COMPOSITIONS OF THE INVENTION

The following assay method was utilized to illustrate the antitumor effectiveness of the indole alkaloid compositions of the invention.

P388 MOUSE LEUKEMIA CELL ASSAY

Maintenance of Cell Line

P388 mouse leukemia cells are grown in Dulbecco MEM medium with 10% horse serum, 4 mM glutamine, and 20 ug/ml gentamycin (Biologos, Inc.). Cells are incubated in 10% $CO_2$ and subcultured 2 times per week.

PROCEDURE

1. Add composition to each well of a 24-well plate or tube and allow solvent to evaporate to dryness.
2. Add 2 ml ($1.2 \times 10^5$) cells to each well or tube and mix.
3. Incubate in 10% $CO_2$ at 37° for 48 hours.
4. Read plates with an inverted microscope, scoring activity from 1+ to 4+ as follows: ND (not detectable), >90%; 1+, 75–90%; 2+, 50–74%; 3+, 25–49%; 4+, <25% of control growth. Alternatively, the activity may be designated as $IC_{50}$ concentration which is the concentration of composition required to inhibit 50% of cell growth on the plate.

Cell counts are performed on each tube and results are reported as percent of control.

HUMAN TUMOR CELL LINE ASSAY

Maintenance of Cell Line HCT-8 human colon tumor cells are grown in RPMl 1640 medium (GIBCO). A-549 human lung carcinoma cells and MD-AMB-231 human breast cancer cells are cultured in Dulbecco medium (Biologos, Inc.). All media are supplemented with 10% fetal bovine serum and contain 50 ug/ml gentamycin. All human tumor cell lines are incubated at 5% $CO_2$ at 37° and subcultured once a week. The seeding levels are 350,000 MCF-7 cells, 60,000 HCT-8 cells and 300,000 A-549 cells per T-25 Flask. Vinblastine is used as a positive control.

PROCEDURE

1. Seed 1ml cell (5000 HCT-8, 8000 A-549, 12000 MD-AMB-231) in each well of a 24-well plate.
2. Incubate in a $CO_2$-incubator for 48 hours.
3. Add composition to each well and incubate for an additional 120 hours.
4. Discard medium and stain with methylene blue (HCT-8) or crystal violet (A-549 and MD-AMB-231).
5. Compare cell density of drug-treated well with that of the control (no drug added) as follows: ND (not detectable), >90%; 1+, 75–90%; 2+, 50–74%; 3+, 25–49%, 4+, >25% of control growth.

Positive control Vinblastine in aqueous solution at the following concentrations.

| Solution Conc. | Amt added | Final conc. in test |
|---|---|---|
| 5 mg/ml | 2 μl | 5 μg/ml |
| 1 mg/ml | 2 μl | 1 μg/ml |
| 0.1 mg/ml | 2 μl | 0.1 μg/ml |
| 0.05 mg/ml | 2 μl | 0.05 μg/ml |

The results of the above assays are summarized in Table 1.

TABLE 1

Antitumor Activity of Biemnidin (1)
Mouse: P388: $IC_{50}$ = 15 μg/l

| Human: | Tumor | Cell Line | Activity at prescribed doses (μg/ml) | | |
|---|---|---|---|---|---|
| | | | 50 | 10 | 1 |
| | Colon | HCT-8 | 4+ | 4+ | ND |
| | Lung | A-549 | 4+ | 4+ | ND |
| | Mammary | MD-AMB-231 | 4+ | 4+ | ND |

The above data reports the in vitro activity of the compositions of the invention for inhibiting tumors. The above results indicate, as would be known to those skilled in the art, that the composition biemnidin and the other indole alkaloid compositions of the invention are useful for inhibiting tumors in vivo in hosts, including mammals, and for treating diseases caused thereby.

The scope of the present invention is not limited by the description, examples, and suggested uses herein and modifications can be made without departing from the spirit of the invention. Derivatives of the compositions of the invention such as chloride derivatives may be prepared which may have antitumor activities. The composition described herein may have other useful applications such as, for example, analgesic applications or as starting materials for the preparations of other compositions. Therapeutic application of the compositions of the present invention can be accomplished by any suitable therapeutic method and technique as is presently or prospectively known to those skilled in the art. Further, the composition of the invention may have use as a starting material or intermediate for the preparation of other useful compositions. Thus, it is intended that the present invention cover the modifications and variations of this invention provided that they come within the scope of the appended claims and their equivalents.

What is claimed is:

1. A substantially pure compound according to the formula:

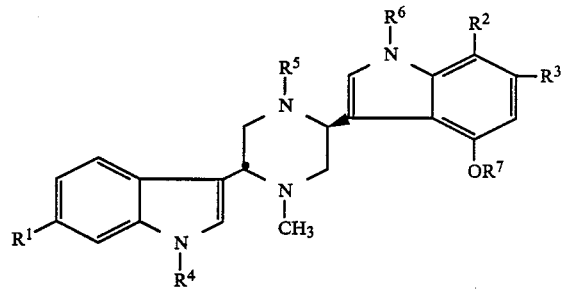

wherein $R^{1-3}$ are the same and are hydrogen or halogen, $R^{4-7}$ are the same and are —H, —R or —COR, and R is lower alkyl.

2. A compound of claim 1 wherein $R^{1-3}$ are hydrogen or bromine and $R^{4-7}$ are —H, —$CH_3$ or —$COCH_3$.

3. A substantially pure compound of claim 1 according to the formula:

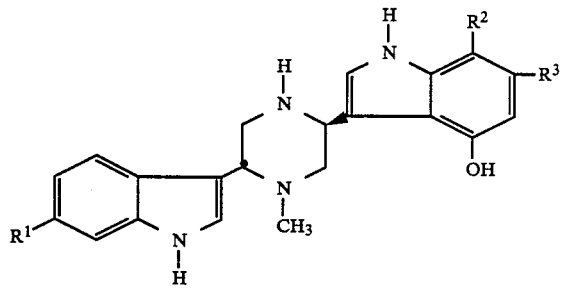

wherein $R^{1-3}$ are the same and are hydrogen or bromine.

4. A substantially pure compound of claim 1 according to the formula:

5. A pharmaceutical composition containing an effective antitumor amount of one or more of the compounds of the formula:

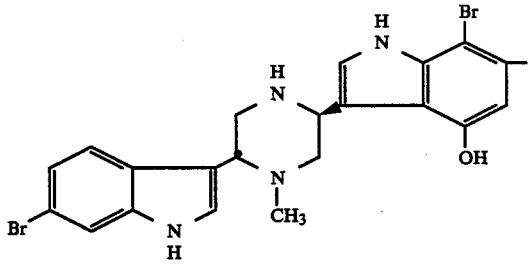

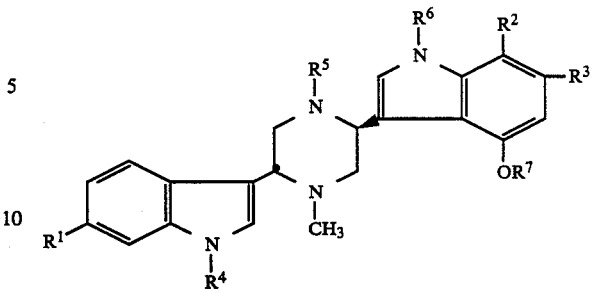

wherein $R^{1-3}$ are the same and are hydrogen or halogen, $R^{4-7}$ are the same and are —H, —R or —COR, and R is lower alkyl and a non-toxic pharmaceutically acceptable carrier or diluent.

6. A pharmaceutical composition containing an effective antitumor amount of one or more of the compounds of claim 2 and a non-toxic pharmaceutically acceptable carrier or diluent.

7. A pharmaceutical composition containing an effective antitumor amount of one or more of the compounds of claim 3 and a non-toxic pharmaceutically acceptable carrier or diluent.

8. A pharmaceutical composition containing an effective antitumor amount of one or more of the compounds of claim 4 and a non-toxic pharmaceutically acceptable carrier or diluent.

* * * * *

UNITED STATES PATENT AND TRADEMARK OFFICE
CERTIFICATE OF CORRECTION

PATENT NO. : 4,895,844

DATED : January 23, 1990

INVENTOR(S) : Shigeo Komoto, Oliver J. McConnell

It is certified that error appears in the above-identified patent and that said Letters Patent is hereby corrected as shown below:

Abstract: last 2 words: "Biemnidae" should read --*Dragmacidon sp.*--.

Column 1: line 13: "Oragmacidon" should read --*Dragmacidon*--; line 28: "cachexia" should read --cachexia.--.

Column 2: line 18: "methyl acetyloxy should read --methyl or acetyloxy--.

Column 4: line 48: "sulfoxide and" should read --sulfoxide, methanol, and--.

Column 5: line 6: "acetate benzene" should read --acetate, benzene--.

Column 6: line 23: "CHC13" should read --$CHCl_3$--.

Signed and Sealed this

Sixteenth Day of July, 1991

Attest:

HARRY F. MANBECK, JR.

Attesting Officer

Commissioner of Patents and Trademarks